United States Patent [19]

Mitchell et al.

[11] Patent Number: 5,590,648
[45] Date of Patent: Jan. 7, 1997

[54] PERSONAL HEALTH CARE SYSTEM

[75] Inventors: Andrew Mitchell, Wilmington; Joseph L. Lardear, Newark; Dave I. Schonbach, Hockessin, all of Del.

[73] Assignee: Tremont Medical, Aston, Pa.

[21] Appl. No.: 224,444

[22] Filed: Apr. 7, 1994

Related U.S. Application Data

[63] Continuation-in-part of Ser. No. 982,993, Nov. 30, 1992, abandoned.

[51] Int. Cl.$^6$ .................... A61B 5/00; A61M 5/00
[52] U.S. Cl. ................ 128/630; 128/670; 128/671; 128/716; 128/200.24; 364/413.02; 364/413.27; 604/19
[58] Field of Search ........................ 128/630, 668, 128/670–2, 687, 700, 736, 716, 903–4, 200.24, 204.18; 604/19; 364/413.02, 413.03, 413.27

[56] References Cited

U.S. PATENT DOCUMENTS

| | | |
|---|---|---|
| 3,762,398 | 10/1973 | Schefke et al. ............... 128/630 |
| 3,857,383 | 12/1974 | Sommerfeld et al. . |
| 3,860,000 | 1/1975 | Wootten et al. . |
| 3,870,035 | 3/1975 | Sarnoff ............... 128/904 X |
| 3,894,533 | 7/1975 | Cannon ............... 128/671 |
| 4,291,692 | 9/1981 | Bowman et al. . |
| 4,300,550 | 11/1981 | Gandi et al. . |
| 4,356,486 | 10/1982 | Mount . |
| 4,366,818 | 1/1983 | Izumi . |
| 4,403,984 | 9/1983 | Ash et al. . |
| 4,414,982 | 11/1983 | Durkan ............... 128/716 |
| 4,449,538 | 5/1984 | Corbitt et al. . |
| 4,494,950 | 1/1985 | Fischell ............... 128/903 X |
| 4,534,756 | 8/1985 | Nelson . |
| 4,584,989 | 4/1986 | Stith . |
| 4,710,165 | 12/1987 | McNeil et al. . |
| 4,715,385 | 12/1987 | Cudahy et al. . |
| 4,803,625 | 2/1989 | Fu et al. . |
| 4,813,427 | 3/1989 | Schlaefke et al. ............... 128/671 |
| 4,832,033 | 5/1989 | Maher et al. ............... 364/413.27 |
| 4,889,131 | 12/1989 | Salem et al. ............... 128/903 X |
| 4,916,441 | 4/1990 | Gombrich . |
| 4,957,121 | 9/1990 | Icenogle et al. . |
| 5,036,852 | 8/1991 | Leishman ............... 128/904 X |
| 5,088,981 | 2/1992 | Howson et al. . |
| 5,101,820 | 4/1992 | Christopher . |
| 5,142,484 | 8/1992 | Kaufman et al. ............... 128/630 |
| 5,343,869 | 9/1994 | Pross et al. . |
| 5,375,604 | 12/1994 | Kelly et al. . |
| 5,417,222 | 5/1995 | Dempsey et al. . |

FOREIGN PATENT DOCUMENTS 2215331  10/1973  Germany ............... 128/630

Primary Examiner—Lee S. Cohen
Attorney, Agent, or Firm—Panitch Schwarze Jacobs & Nadel, P.C.

[57] ABSTRACT

A personal health care system utilizing a unitary command center having a computer for receiving, storing, processing, and transmitting information, and a plurality of interfacing ports. Each interfacing port is adapted to accept a plurality of different patient monitoring sensor modules, a plurality of different accessory modules, and a plurality of different therapy-providing modules. An accepted module is electrically interconnected to the data processor for sending and receiving information therebetween. The data processor includes means for providing operating instructions to the sensor modules, accessory modules, and therapy-providing modules. Each sensor module senses and provides information on a condition of a patient and each therapy-providing module provides a therapy to the patient. The data processor monitors the information provided by the sensor modules and controls provision of the therapy to the patient.

33 Claims, 7 Drawing Sheets

PERSONAL HEALTH CARE SYSTEM

This is a continuation-in-part of U.S. Patent application Ser. No. 07/982,993, filed Nov. 30, 1992, now abandoned.

FIELD OF THE INVENTION

The present invention relates to the field of providing health care for patients.

BACKGROUND OF THE INVENTION

Care of the ailing elderly and other bedridden or partially bedridden patients often requires the monitoring of several health parameters, as well as treatment of one or more indications. Hospitalization of such patients is very expensive. Cost containment with maintenance of quality care is a major focus for the health care industry. Given the great cost of hospital space, increasing demands are being made to move patients as soon as possible from a hospital through perhaps some intermediary care-giving recovery facility, such as a nursing home, to the home itself. Often the patient is moved before he or she is ambulatory or capable of being removed from life-support apparatus and specialized equipment has been developed for such moves, U.S. Pat. Nos. 4,957,121 and 4,584,989 describing examples of such equipment.

Various devices for patient monitoring and/or treatment in the hospital or home care setting are known in the art.

U.S. Pat. No. 5,101,820 discloses a bedside unit for supplying oxygen, and U.S. Pat. No. 4,300,550 discloses a combination oxygenating and aspirating device.

U.S. Pat. Nos. 4,403,984, 4,449,538, 4,534,756 and 5,088,981 disclose various controlled infusion systems.

U.S. Pat. No. 4,366,818 discloses a vacuum type urinating aid.

U.S. Pat. No. 4,710,165 discloses a suction/collection device that can be hung at a patient's bedside.

U.S. Pat. No. 3,857,383 discloses a health screening unit including testing equipment.

Frequently, several types of monitoring and therapeutic devices are needed to maintain a home-bound patient, such as a monitoring unit described by Fu and Manning (U.S. Pat. No. 4,803,625), a feeding and aspirating unit such as described by Wooten and Rives (U.S. Pat. No. 3,860,000) and a drug infusion unit such as described by Bowman and Westenkow (U.S. Pat. No. 4,291,692). Such an array of separate devices is bulky, cumbersome, difficult to set-up and maintain, and confusing to use by an unskilled caregiver. The multiplicity of power cords, monitoring displays, alarms and related circuitry presented by individualized units makes their placement and access a problem. Access to the patient can be a problem as well. Additionally, these separate devices are usually rented or purchased and serviced by different dealers.

In short, no system has been provided in the prior art which is well adapted for use in home health care, sub-acute care, and/or assisted care which solves all of the aforementioned problems and drawbacks with a compact, integrated, self-contained unit.

There remains a need in the art for improved systems for the treatment and monitoring of ailing elderly and other bedridden or partially bedridden patients, particularly in the home health care setting.

SUMMARY OF THE INVENTION

In accordance with the present invention, a personal health care system comprises a command center including computer means for receiving, storing, processing, and transmitting information. Means are provided for supplying electrical power to the system, the power supply means comprising means for connecting to an outside source of electrical power, battery means for storing and delivering electrical power, or a combination thereof. Means are also provided for connecting the computer with a plurality of patient monitoring modules, wherein the computer monitors information on the patients condition which is received from the monitoring modules. The plurality of monitoring modules are selected from a breathing rate sensor, a pulse rate sensor, a body temperature sensor, a blood pressure sensor, a urinary discharge volume sensor and an oximeter, among others. Means are included for providing an alert concerning the patient's condition, the alerting means comprising an alarm, means for electronically communicating with a remote monitoring service, or a combination thereof. Additional means are provided for connecting the computer with a plurality of modules for providing therapy to the patient, wherein the computer controls provision of the therapy to the patient. The therapy-producing module is selected from means for assisting the patient's breathing, means for delivering medication to the patient, means for delivering nutrition to the patient and means for receiving and removing urine from the patient, among others.

DETAILED DESCRIPTION OF THE PREFERRED EMBODIMENT

With reference to the drawings, a personal health care system in accordance with the present invention includes a unitary command center 10, having a means for receiving, storing and processing information such as computer 12.

Figure 1:
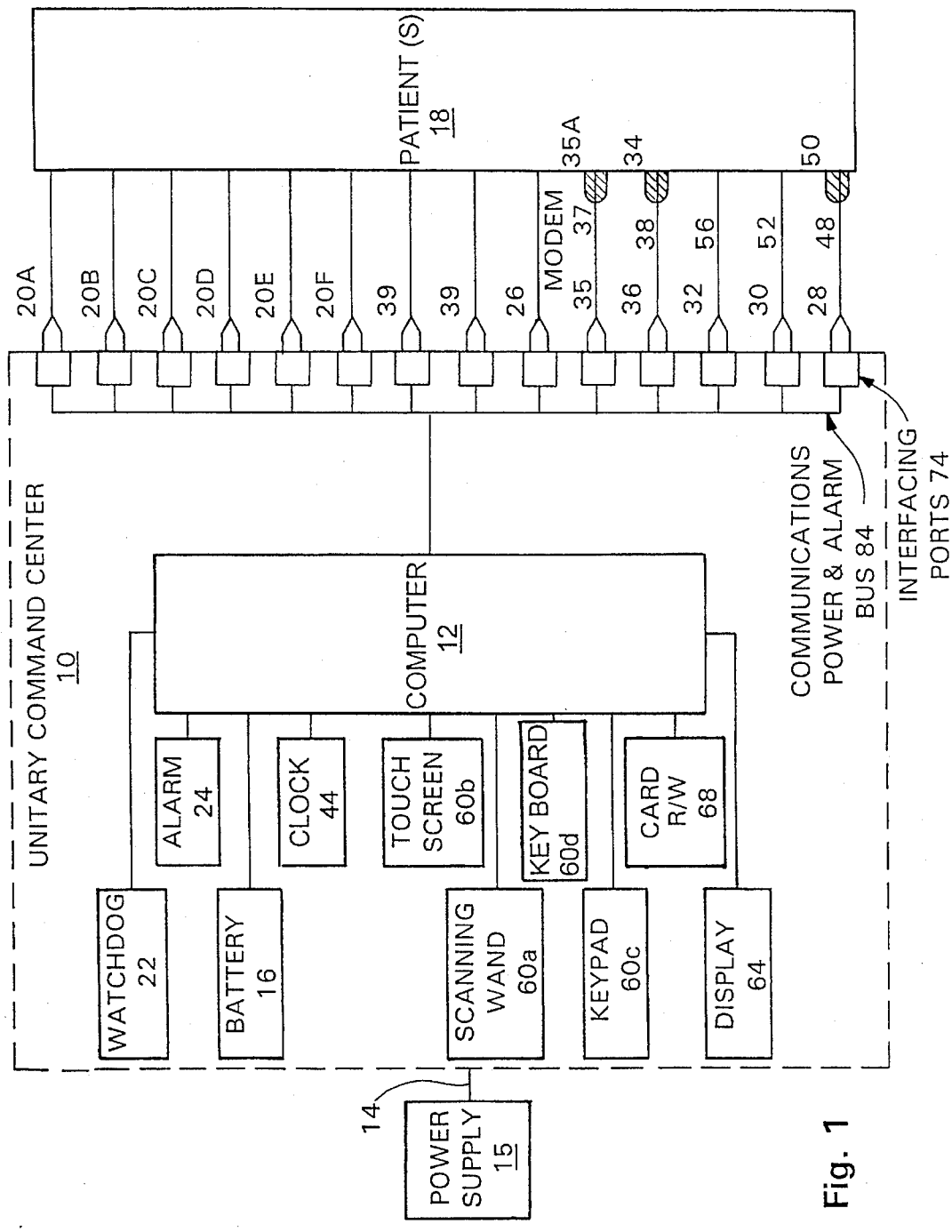
FIG. 1 is a block diagram including a personal health care system in accordance with one embodiment of the present invention.

Unitary command center 10 includes means for supplying electrical power to the system. The power supply means can comprise a power supply cable 14 for connecting to an external source of electrical power such as AC house current. A battery 16 for storing and delivering electrical power to the system, or in preferred embodiments, a combination thereof is shown in FIG. 1. With the combination power supply system shown in FIG. 1, battery 16 acts as a backup in the event of an external power failure.

In the embodiment shown, all power to the personal health care system of the present invention is through unitary command center 10 by means of power supply cable 14 or battery 16. In accordance with the embodiment, unitary command center 10 supplies all power to the below-described peripherals, patient monitoring sensor modules and therapy-providing modules.

Unitary command center 10 is connected to a plurality of patient monitoring sensor modules for monitoring the health parameters and condition of a patient 18. In preferred embodiments, the patient-monitoring sensor modules are detachably connectable to unitary command center 10 via an interfacing port 74. The plurality of sensor modules connected to patient 18 can include a breathing rate sensor 20*a*, pulse rate sensor 20*b*, body temperature sensor 20*c*, blood pressure sensor 20*d*, urinary discharge volume sensor 20*e*, oximeter 20*f*, an ECG sensor module, an EKG sensor module, an EEG sensor module, an oxygen analyzer module, a fetal monitor module, a dental patient monitoring module, and a multi-gas analyzing module.

Breathing rate sensor module 20*a* can be any suitable breathing rate sensor, such as those incorporating a hollow tube fastened about the patient's chest. Pulse rate sensor 20*b* can be any suitable pulse rate sensor, such as pulse rate sensors which are presently well known in the art. Body temperature sensor 20*c* can be any suitable body temperature sensor, such as those which are presently known in the art. The blood pressure sensor 20*d* can be any suitable blood pressure sensor, including blood pressure sensors which are well known in the art. The urinary discharge volume sensor 20*e* can be any suitable means for measuring urinary discharge volume. Suitable urinary discharge volume sensors include those which measure the weight of the urinary liquid. Oximeter 20*f* can be any suitable oximeter means, including oximeters which are presently known in the art.

In addition to the sensor modules described above, any number of other patient monitoring sensor modules can be included in the present personal health care system.

A personal health care system in accordance with the present invention includes an alerting device for providing an alert concerning the patient's condition. The alerting means can comprise an alarm 24, which can be an audible and/or visible alarm, and/or means for electronically communicating with a remote monitoring service, such as a radio-frequency communication device, or modem 26. In the embodiment shown in FIG. 1, the personal health care system of the invention includes both an audible alarm 24 and modem 26. Modem 26 automatically dials for an ambulance or other professional assistance in the event of an emergency condition, and/or can provide information on the patients condition to an off-site patient monitoring service. The modem 26 may be supplemented with or replaced by a direct connection to a peripheral device, a local network, and/or an electromagnetic transmission means.

In accordance with the present invention, a plurality of modules for providing therapy to patient 18 are electrically interconnected to computer 12 via an interfacing port 74.

The therapy-providing module can be a means 28 for assisting the patient's breathing, a means 30 for delivering medication to the patient, a means 32 for delivering nutrition to the patient, a means 36 for receiving and removing urine from the patient, and/or other means. Any other suitable modules for providing therapy to the patient can be provided, such as a heat pad module 35 connected to heat pad 35*a* via line 37.

The aforementioned therapy-providing modules may perform the following functions: maintaining blood sugar, providing electric nerve stimulation, providing physical therapy, providing insulin, ventilating, nebulizing, providing chemotherapy, injecting via a syringe, humidifying, respirating, and operating a heating pad, as well as many other functions that would be apparent to one skilled in the art.

In preferred embodiments, the personal health care system of the present invention includes a plurality of the therapy-providing modules, and the therapy-providing modules are detachably connectable to unitary command center 10.

The provision or dispensing of therapy by the therapy-providing modules of the present invention is controlled by computer 12. In preferred embodiments, the provision or dispensation of therapy can be based on information received by computer 12 from one or more patient monitoring sensor modules. For example, dispensation of a heart drug to the patient by medication-providing module 30 can be controlled by computer 12 based on information on the patient's pulse and/or blood pressure received by computer 12 from pulse rate sensor 20*b* and blood pressure sensor 20*d*, respectively.

In the embodiment shown, the means for receiving and removing urine from the patient is a suction pump. An external urinary catheter 34 is connected to the suction pump 36 via tube 38. Pump 36 is activated by computer 12 in response to a discharge of urine by patient 18, which is detected by the urinary discharge monitoring sensor module 20*e*.

In the preferred embodiment, the means 28 for assisting the patient's breathing can be a respirator, ventilator, continuous positive airway pressure (CPAP) device, nebulizer, humidifier or $O_2$ concentrator. When the breathing assistance means 28 is a respirator, ventilator or CPAP device, it can be controlled by computer 12 based on monitoring of breathing rate sensor 20*a*.

The means 28 for assisting the patient's breathing provides oxygen to the patient via line 48, and mask or nasal prongs 50.

In the embodiment shown, the means for delivering medication to the patient is comprised of an infusion pump 30, connected to the patient 18 via an intravenous or intramuscular line 52.

in the illustrated embodiment, the means for delivering nutrition to the patient is comprised of a nutrition pump 32 which delivers nutrition to the patient via enteral line 56.

In the embodiment shown, the unitary command center 10 includes a clock 44, connected to computer 12 by 46. Computer 12 can compare information received from the monitoring modules against clock 44 when computer 12 is processing information from the monitoring modules. For example, the breathing rate monitoring module 20*a* can be utilized to monitor apneic episodes of the patient by comparing the patient's breathing rate against clock 44. When the means 28 for assisting the patient's breathing is a CPAP device, computer 12 can increase the air pressure of the CPAP if sensor 20*a* indicates that breathing has stopped for a specified period of time as measured by clock 44. After breathing is restored to a normal rate, the CPAP returns to its normal setting under the control of computer 12.

Computer 12 can also utilize clock 44 to time infusion of drug(s) by pump 30, as well as delivery of nutrition by pump 32. The clock 44 can also be used for timed control of heat pad 35a and/or the nebulizer or humidifier.

In preferred embodiments, unitary command center 10 includes means for diagnostic analysis of the personal health care system. In accordance with this embodiment, the alert means (alarm 24 and modem 26) includes means for providing an alert concerning malfunction of the system in response to a malfunction signal outputted from the diagnostic analysis means.

In preferred embodiments, the personal health care system of the present invention includes a plurality of accessory modules. Such accessory modules include but are not limited to a urine collection module, a water module providing drinking water to the patient, a suction pump removing a fluid from the patient, a vision testing module, a breast pump module, a hearing test module, an eye motion detecting module, a printer module, an intercom module, a networking module, a modem module, a magnetic card reading module, a voice recognition module, a memory card reading module, a strip chart recording module, and a telephone module.

However, one skilled in the art will recognize that a plurality of other different devices and accessories may be attached to the personal health care system in order to further enhance patient care. Moreover, one skilled in the art will recognize that a module listed as an accessory may in certain circumstances be considered to be a monitoring device or to be a therapy-providing device.

Figure 2:
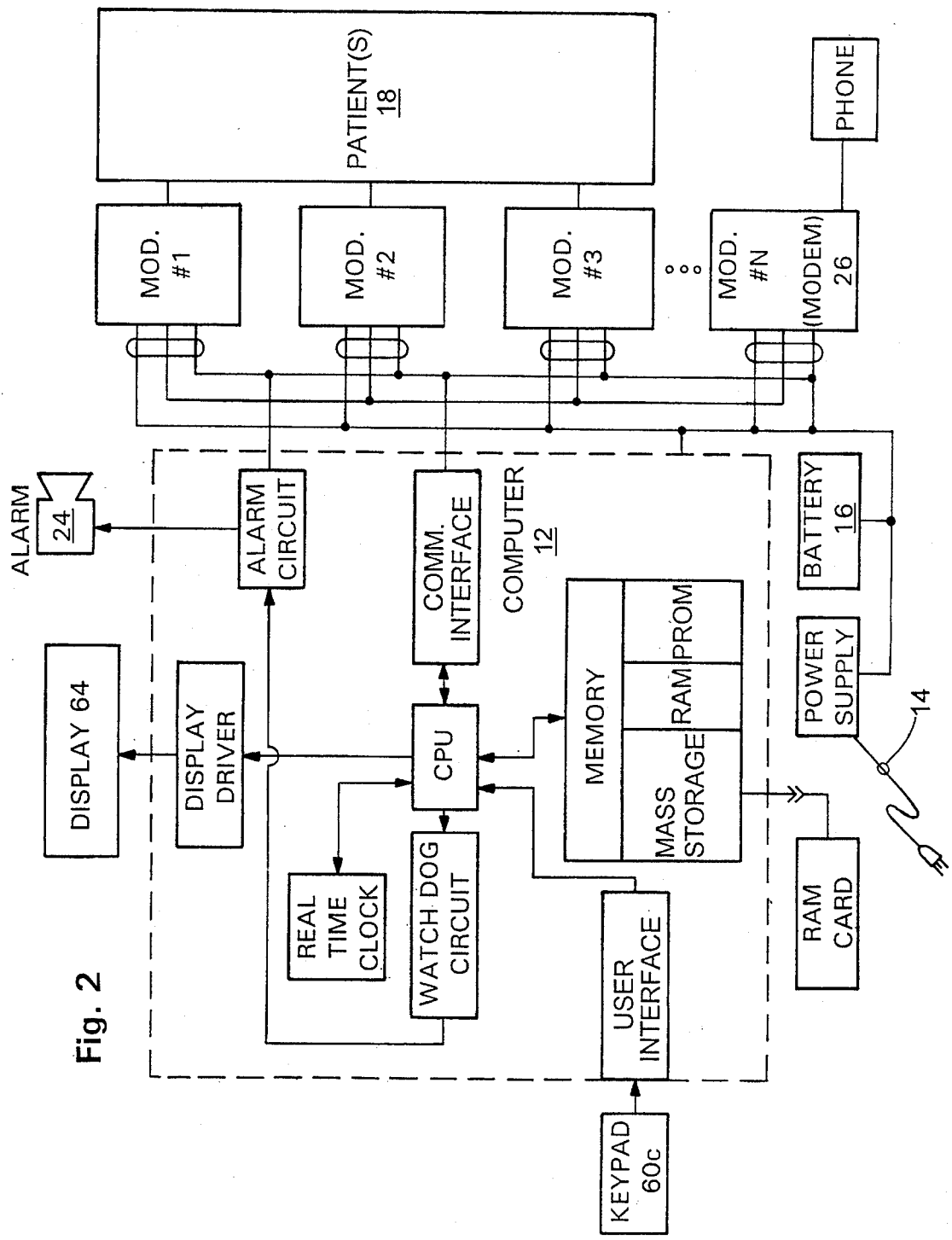
FIG. 2 is a block diagram showing independent power, alarm, and communications channels for enhancing reliability of a personal health care system in accordance with the present invention.
Figure 3:
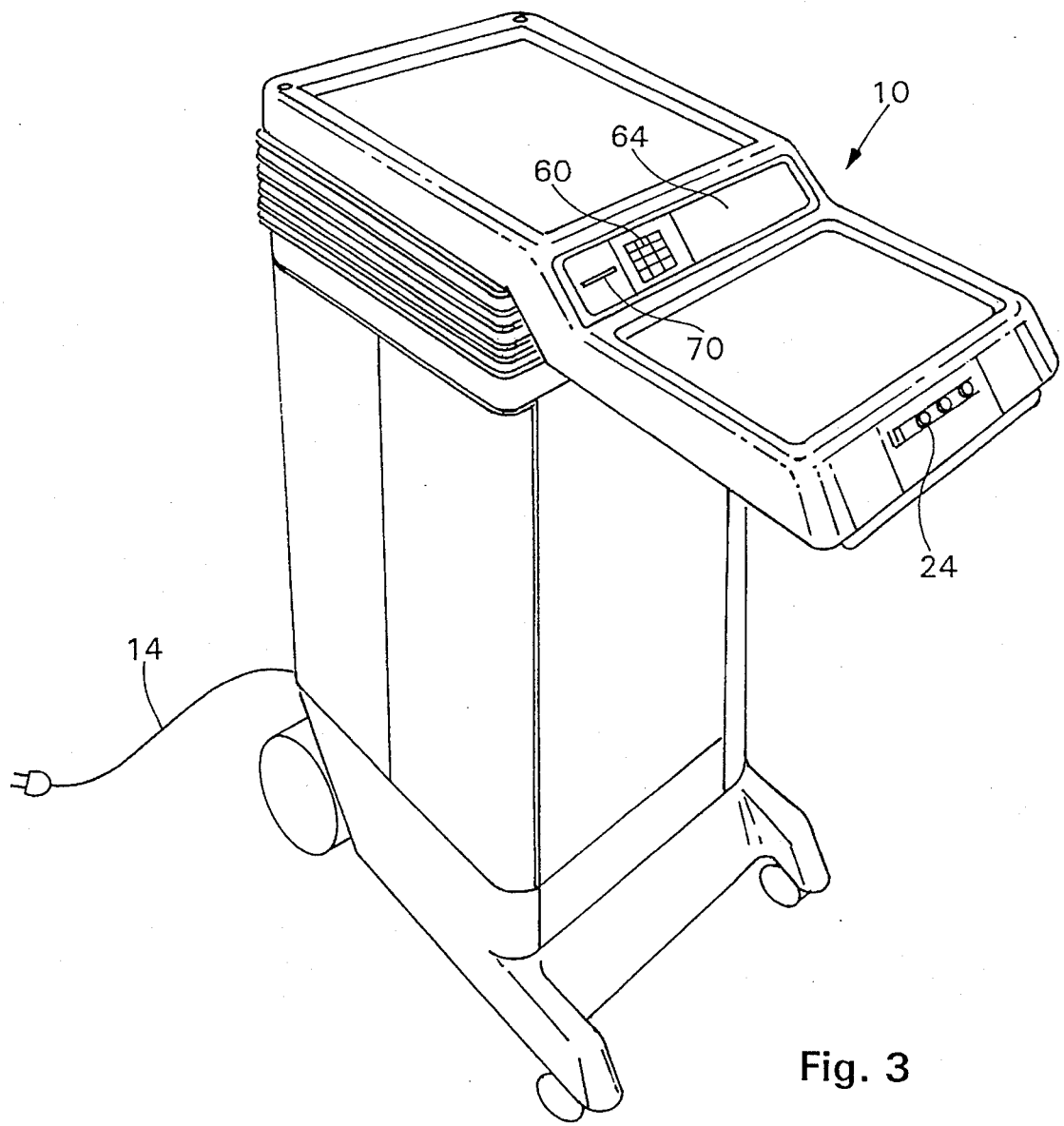
FIG. 3 is a perspective view of a personal health care system command center in accordance with one embodiment of the invention.
Figure 4:
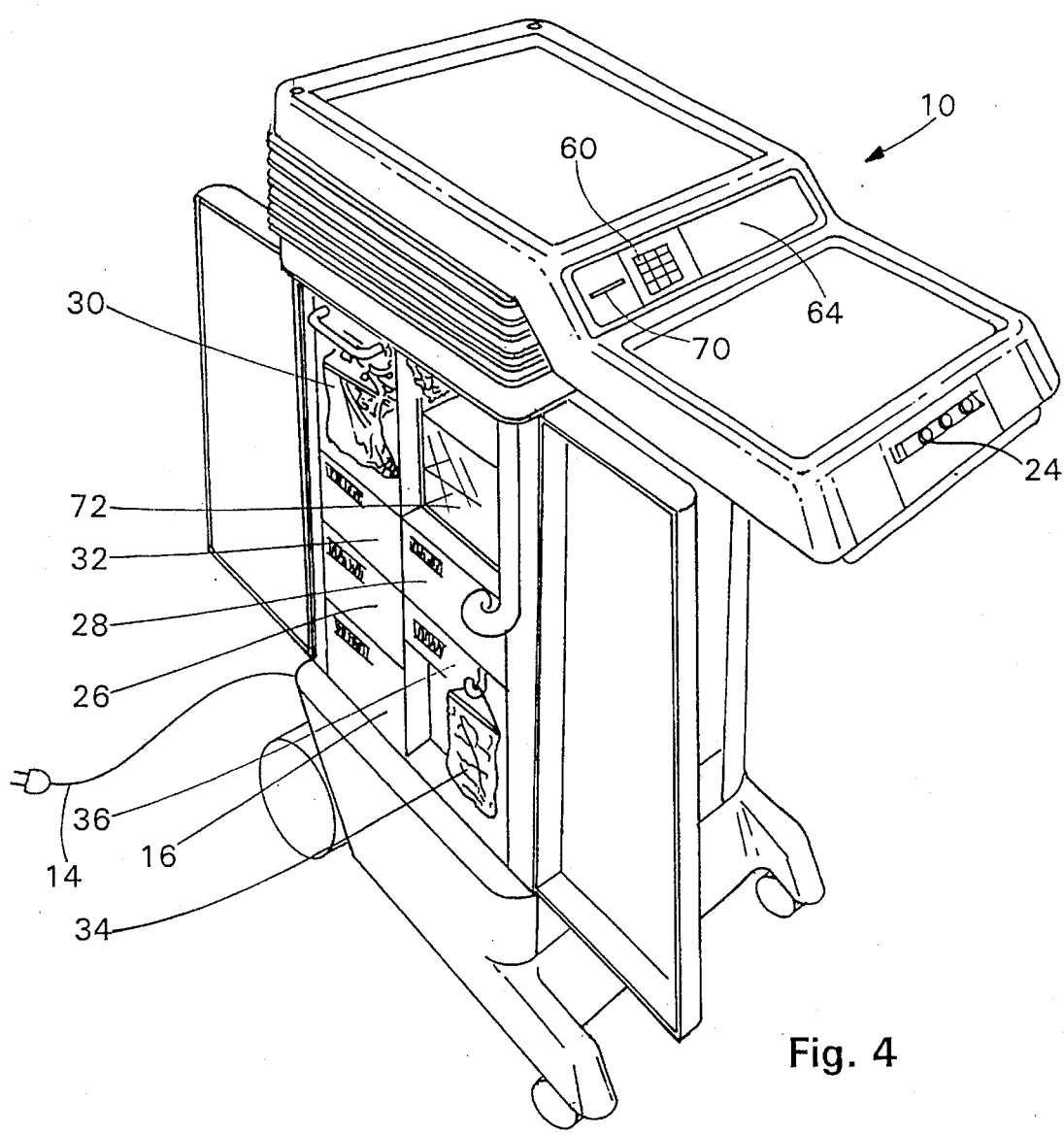
FIG. 4 is a perspective view of the command center of FIG. 5 with side portions opened for access.
Figure 5:
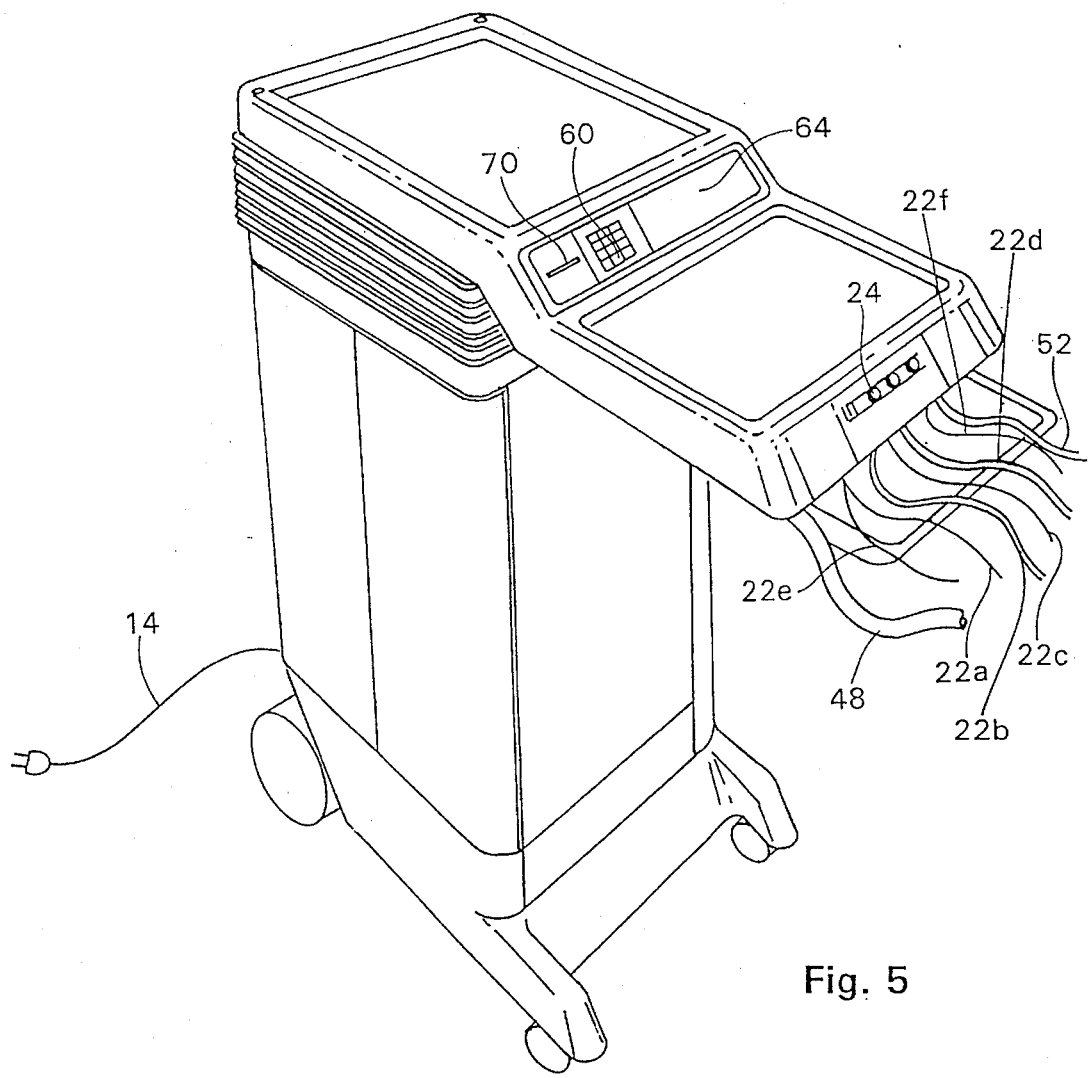
FIG. 5 is a perspective view of the command center of FIGS. 3 and 4 showing lines for connecting to a patient.

FIG. 2 illustrates a command center which exchanges, controls and alarms information with the various therapeutic and monitoring sensor modules.

The heart of the computer means 12 is a central processing unit (CPU). FIG. 2 also illustrates control circuitry and local memory. During normal operation, the CPU is under control of the primary microprocessor. If, however, a failure is detected by the microprocessor monitoring hardware or watchdog 22, an alert will be issued via the alarm 24 and/or modem 26.

In the embodiment shown in FIG. 1, unitary command center 10 includes means for inputting information into the computer, such as a scanning wand 60a for reading bar codes, a trackball, a mouse, a magnetic card reader, an optical card reader, a microphone, a touch sensitive data screen 60b, key 60c and a keyboard 60d, connected to computer 12. However, one skilled in the art will recognize that other inputting means may be employed. The means for inputting information may be employed to provide a security feature preventing unauthorized access to the unitary command center 10. Additionally, unitary command center 10 includes display means 64 for displaying information which is input into, received by and stored by or processed by computer 12. Also shown may be a PCMCIA card read/write unit 68, connected to computer 12.

Figure 7:
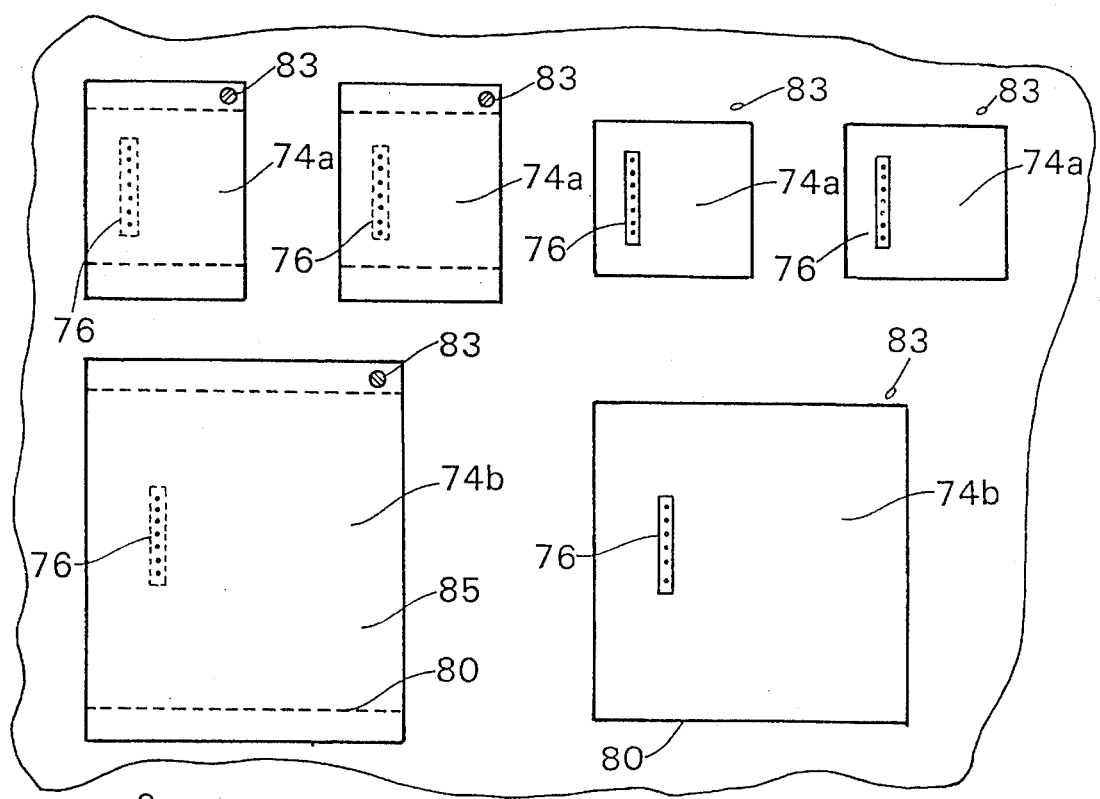
FIG. 7 is a perspective view of a portion of the command center of FIG. 3 showing several unoccupied interfacing ports and several interfacing ports accepting modules and electrically interconnecting the modules with the personal health care system.

As can be seen in FIGS. 1 and 7, the unitary command center 10 preferably includes a plurality of interfacing ports 74, 74a, 74b for accepting the patient monitoring sensor modules, the accessory modules, and the therapy-providing modules. Four smaller size ports 74a and two larger size ports 74b are shown in FIG. 7. While two sizes are seen, one skilled in the art will recognize that one, three, four or any other number of sizes of ports may be provided.

As seen in FIG. 7, each interfacing port includes an electrical connector 76 for electrically interconnecting an accepted module to the computer 12. Correspondingly, and as may be seen in FIGS. 8 and 9, each patient monitoring sensor module, each accessory module, and each therapy-providing module includes a mating electrical connector 78 positioned and sized to interconnect with an electrical connector 76. As one skilled in the art will recognize, the electrical connectors 76, 78 may be selected from any of a variety of known electrical connectors.

Figure 8:
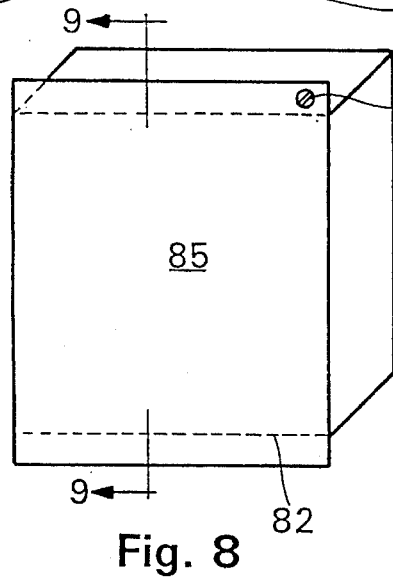
FIG. 8 is a perspective view of a typical system module.

Preferably, a plurality of the interfacing ports have a common first physical outline 80 (as seen in FIG. 7) and the interfacing side of each of a plurality of the sensor modules, accessory modules, and therapy-providing modules has a complementary common second physical outline 82 (as seen in FIG. 8). Also preferably, each interfacing port also has a mounting and retaining means 83 to permit any sensor module, accessory module, or therapy-providing module 85 having the proper physical outline to be mounted and retained in a corresponding interfacing port 74. For example, the mounting and retaining means 83 could comprise ¼ turn fasteners for locking the module into the interfacing port and holding the module therein. However, one skilled in the art will recognize that many means for mounting and retaining a module in the interfacing port may be employed. Thus, any sensor module, accessory module, and any therapy-providing module having the second physical outline 82 may be accepted by any interfacing port having the common first physical outline 80 and the mounted module will be electrically interconnected to the computer 12.

Figure 9:
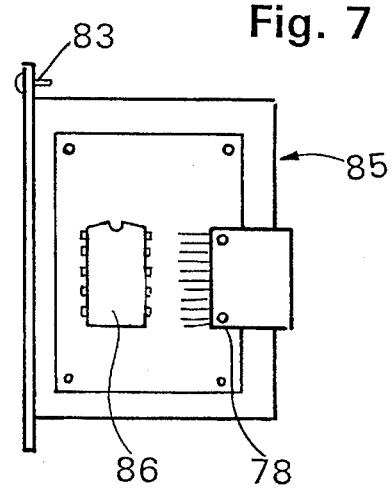
FIG. 9 is a cross-sectional view taken along the line 9—9 of FIG. 8.

As seen in FIG. 1, the unitary command center 10 also includes an electrical bus 84. Preferably, each module has a slave processor 86 (as seen in FIG. 9) electrically connected to the electrical connector 78 and the computer 12 communicates with the slave processor 86 via the bus 84 and the electrical connectors 76, 78. Also preferably, the electrical bus 84 supplies power to the modules from the unitary command center 10 via the electrical connectors 76, 78. As one skilled in the art will recognize, the communications portion of the bus 84 may comprise an RS-485 bus, ethernet or any of a plurality of other buses.

Preferably, the slave processor 86 on each module is adapted to receive information from and provide information to the computer 12 by way of the electrical bus 84. Also preferably, the slave processor controls the operation of the module. Thus, the computer 12 communicates with the slave processor 86 on the module and programs the module to perform in a particular manner.

Preferably, commands to a particular module are transmitted as packets of information originating from the computer 12, and each of the modules electrically interconnected to the computer 12 via the bus 84 listens for packet transmissions. Upon detection of a packet directed to a particular module, the module will formulate a response and transmit it to the computer 12 to acknowledge the reception of a command. Preferably, the computer 12 always initiates communication and each module can only respond to a request for information.

Preferably, each module electrically interconnected to the system 10 is capable of operating independently once programmed by the computer 12. For example, the infusion pump module 30 may be programmed to deliver 20 millimeters of a liquid at a rate of 1 millimeter per hour, and will complete the task without the need for further commands from the computer 12.

Preferably, the bus 84 includes an emergency alarm signal line to allow any module to alert computer 12 of problems encountered. For example, if an air bubble is detected by the infusion pump 30, the pump will cease to operate and will signal the computer 12 that an alarm condition exists. Thereafter, the computer 12 would communicate with the pump module 30 via the bus 84 to discover the exact cause of the problem. Depending on the problem, the computer may then issue an alert via the alarm 24.

Preferably, the computer 12 is self-configuring based upon the modules electrically interconnected to the bus 84 upon start-up. Thus, the computer 12 polls for the existence of a variety of types of modules by way of the bus 84. If a particular type of module is present, the module responds to the poll with an acknowledgment. Once the existence of a type of module is established, the computer 12 homes the existence in an active device table.

Preferably, the computer 12 includes a plurality of module software drivers. Each type of module for use with the system has a corresponding module software driver. The module software drivers are designed as independent code modules allowing each driver to be developed independently of the main operating code for the computer 12. Preferably, the computer 12 contains a device table data structure that contains a list of all possible types of modules as well as the names and/or the locations of the corresponding module software drivers. If a type of module is marked as active during the aforementioned polling process, the computer 12 activates the module software driver corresponding to the module. Thus, the computer 12 employs the module software driver to control the module.

A module software driver contains all of the code required to operate a particular type of module, and comprises a control portion and a user interface portion. The control portion is responsible for programming and communicating with the module, and acts on information supplied through the user interface portion to accomplish the actual module control. The user interface portion is responsible for passing information to the control portion and for displaying information concerning the module on the display 64. Preferably, each module software driver will be assigned an area on the display 64 to show the status of its corresponding module. For example, the module software driver associated with the blood pressure monitoring module 20d will show pulse and pressure in its assigned display area. Preferably, the user interface portion also provides a custom programming display to permit a user to enter module control program parameters via the display 64 and/or inputting device 60a–d.

As should be recognized, the unitary command center 10 of the personal health care system may be one of several slave command centers interconnected via a communications network. Accordingly, a master control center may be utilized to command and control all the slave command centers from one centralized location. The master command center may be one of the command centers 10 or some other unit specifically designed and programmed to command and control all the command centers. Still further, one slave command center in the network may command and control the modules of another slave command center. While information may be electronically transmitted via the communications network between each individual command center and the master command center, it is also envisioned that a recording media may be used to manually transport such information. Such media includes but is not limited to a magnetic recording media, an optical recording media, and a memory card.

Figure 6:
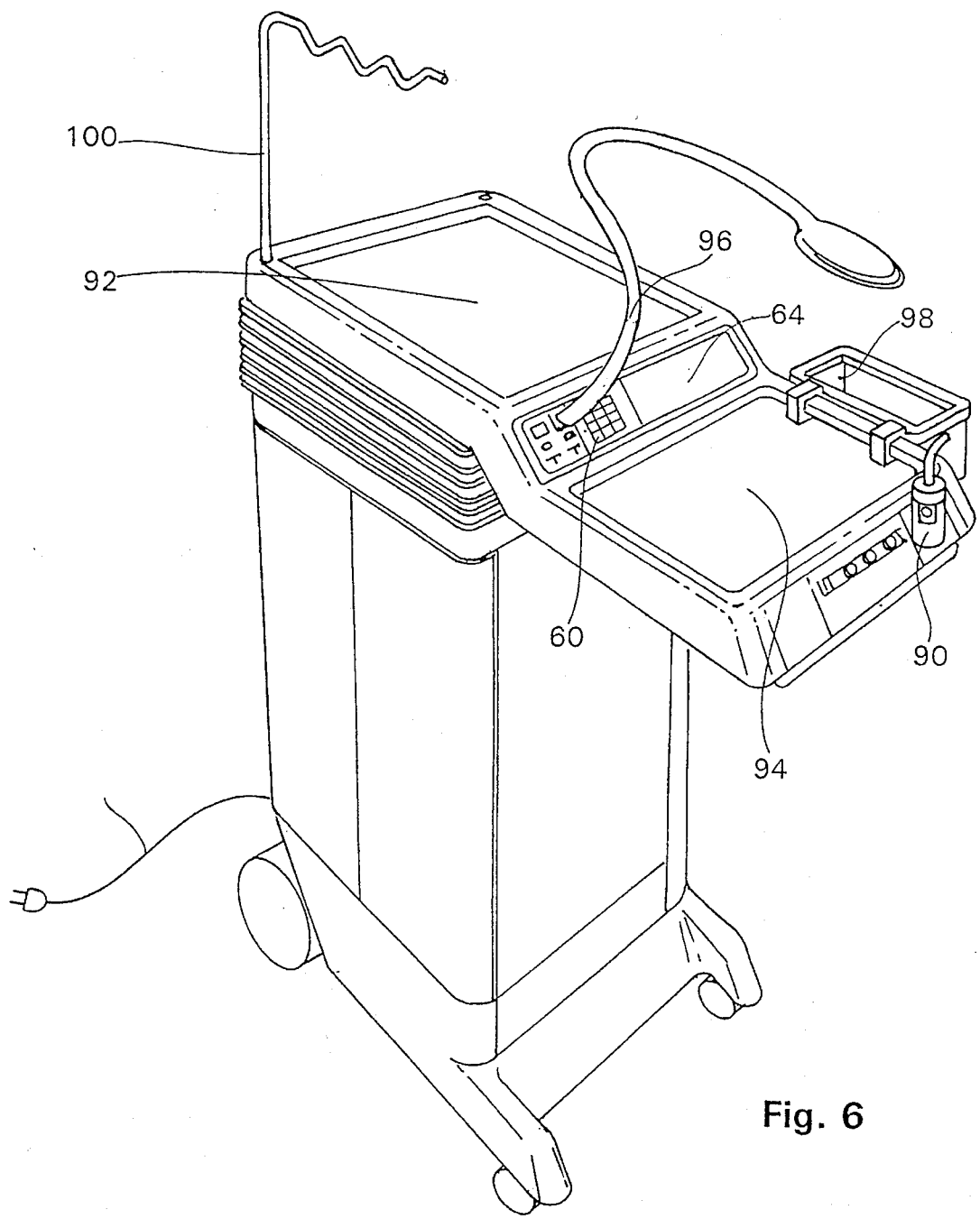
FIG. 6 is a perspective view of a command center in accordance with the invention showing some optional accessories.

In preferred embodiments, unitary command center 10 is easily portable and movable on wheels along with the patient, as shown in FIGS. 3–6. With reference to FIG. 6, the command center can include means 90 for dispensing fresh water with straw, utility table areas 92, 94, 98, a light 96, a waste bin, an IV rack 100, means for storing disposable supplies (not shown), a telephone (not shown) and any other suitable accessory.

The home care patient often requires multiple therapies. It is not uncommon for a stroke patient, for example, to require oxygen, infusion delivery of antibiotic and pain medication, enteral feeding into a gastronomy tube and occasional nasal CPAP. The present invention is capable of providing all these therapies in a single unit located at bedside, eliminating many of the problems associated with the use of multiple non-integrated devices provided by different sources.

Since many modifications, variations, and changes in detail may be made to the described embodiments, it is intended that all material in the foregoing description and accompanying drawings be interpreted as illustrative and not in a limiting sense.

We claim:

1. A personal health care system comprising:

a unitary command center for monitoring a patient and administering therapy to a patient;

a data processor within the unitary command center for receiving, storing, processing, and transmitting information;

a plurality of modules selected from the group consisting of a plurality of different patient monitoring sensor modules, a plurality of different therapy-providing modules, and a plurality of different accessory modules, each module being at least partially contained within a module housing; and a plurality of interfacing ports positioned on the unitary command center and electrically connected to the data processor, each interfacing port for accepting one of the module housings and for electrically interconnecting the module associated with the accepted module housing to the data processor for sending and receiving information therebetween, the data processor including means for providing programming instructions to the associated module for operating the associated module, each sensor module for sensing and providing information on a condition of a patient, the data processor including means for monitoring the information provided by the sensor modules, each accessory module for providing an accessory function, each therapy-providing module for providing a therapy to a patient, the data processor including means for controlling provision of the therapy to the patient.

2. The system of claim 1, wherein at least one of the sensor modules is selected from the group consisting of a breathing rate sensor module, a pulse rate sensor module, a body temperature sensor module, a blood pressure sensor module, a urinary discharge volume sensor module, an oximeter sensor module, an ECG sensor module, an EKG sensor module, an EEG sensor module, an oxygen analyzer module, a fetal monitor module, a dental patient monitoring module, and a multi-gas analyzing module.

3. The system of claim 1 wherein at least one of the accessory modules is selected from the group consisting of a urine pump module, a urine collection module, a module providing drinking water to the patient, a suction pump removing a fluid from the patient, a vision testing module, a breast pump module, a hearing test module, an eye motion detecting module, a printer module, an intercom module, a networking module, a modem module, a magnetic card reading module, a voice recognition module, a memory card reading module, a strip chart recording module, and a telephone module.

4. The system of claim 1, wherein at least one of the therapy-providing modules is selected from the group consisting of means for assisting patient breathing, means for delivering medication to a patient, means for delivering nutrition to a patient, and means for receiving and removing urine from a patient.

5. The system of claim 4, further including the means for assisting patient breathing, said means being selected from the group consisting of a respirator, a ventilator, a continuous positive airway pressure device, a nebulizer, a humidifier, an oxygen concentrator, and a combination thereof.

6. The system of claim 4, further including the means for delivering medication, said means comprising a nebulizer, an infusion pump and a member selected from the group consisting of an intravenous line and an intramuscular line.

7. The system of claim 4, further including the means for delivering nutrition, said means comprising a nutrition pump and an enteral line.

8. The system of claim 4, further including the means for receiving and removing urine, said means comprising an external urinary catheter.

9. The system of claim 8, wherein the means for receiving and removing urine further comprises a container connected to the external urinary catheter for collecting and measuring urine.

10. The system of claim 8, wherein the means for receiving and removing urine further comprises a suction pump fluidly connected to the external urinary catheter for removing urine therefrom and electrically connected to the data processor, and wherein the suction pump is activated by the data processor, the activation in response to a discharge of urine by a patient, the discharge being detected by a urinary discharge monitoring sensor module electrically connected to the data processor.

11. The system of claim 1, further comprising an alerting device electrically connected to and activated by the data processor for providing an alert concerning a condition of a patient, the alerting device being selected from the group consisting of an alarm, means for electronically communicating with a remote monitor, and a combination thereof.

12. The system of claim 11, wherein the alarm is selected from the group consisting of a visible alarm and an audible alarm.

13. The system of claim 11, wherein the means for electronically communicating with a remote monitor is selected from the group consisting of a modem, a direct connection to a peripheral device, a local network, and electromagnetic transmission.

14. The system of claim 11, further including means for diagnostic analysis of the system.

15. The system of claim 14, wherein the means for diagnostic analysis outputs a malfunction signal in response to a malfunction and wherein the alerting device provides an alert concerning a malfunction of the system in response to an outputted malfunction signal.

16. The system of claim 1, further including a power source electrically connected to the unitary command center for supplying electrical power to the system, the power source being selected from the group consisting of a power supply cable for being connected to an outside source of electrical power, a battery, and a combination thereof.

17. The system of claim 16, further including the plurality of different patient monitoring sensor modules, the plurality of different accessory modules, and the plurality of different therapy-providing modules, the power source providing power to the patient monitoring sensor modules and to the therapy-providing modules via the interfacing ports.

18. The system of claim 1, wherein a plurality of the interfacing ports have a common first physical outline and wherein a plurality of the module housings have a complementary common second physical outline with respect to the first physical outline, any module housing being accepted by any interfacing port when the first and second physical outlines are matched, every interfacing port further having retaining means to retain an accepted module housing in place.

19. The system of claim 1, wherein the data processor includes a plurality of module software drivers accessible by the data processor, each module software driver corresponding to at least one of the modules, the data processor having means for determining whether a particular module is electrically interconnected thereto, and for controlling the particular module via the corresponding module software driver.

20. The system of claim 19, wherein each module software driver comprises a control portion and a user interface portion, the control portion adapted to allow the data processor to program and communicate with the particular module and the user interface portion adapted to allow a user to pass information concerning the particular module to the data processor and to display information concerning the particular module on a display.

21. The system of claim 1, wherein each interfacing port includes electrical connectors connected to an electrical bus of the unitary command center and each module includes corresponding electrical connectors connected to a slave processor, the slave processor adapted to receive information from and provide information to the data processor via the electrical bus and electrical connectors and to control the operation of the module.

22. The system of claim 1, wherein the unitary command center includes an inputting device electrically connected to the data processor for inputting information into the data processor.

23. The system of claim 22, wherein the inputting device is selected from a group consisting of a scanning wand for reading bar codes, a trackball, a mouse, a magnetic card reader, an optical card reader, a microphone, a touch-sensitive data screen, a keypad, and a keyboard.

24. The system of claim 22, further including a display electrically connected to data processor for displaying information from the data processor including data input into, received by, stored by and processed by the data processor.

25. The system of claim 1, further including a clock electrically connected to the data processor, the data processor being adapted to compare the clock with information received from the sensor modules when the data processor is processing information from the sensor modules.

26. The system of claim 25, further including a breathing rate sensor module electrically connected to the data processor, the data processor being adapted to compare the clock with breathing rate information received from the breathing rate sensor module for monitoring apneic episodes of a patient.

27. The system of claim 1, further including at least one of the patient monitoring sensor modules.

28. The system of claim 1, further including at least one of the therapy-providing modules.

29. The system of claim 1, further including at least one of the accessory modules.

30. The system of claim 1, further including the plurality of patient monitoring sensor modules, the plurality of accessory modules, and the plurality of therapy-providing modules, wherein the plurality of patient monitoring sensor modules, the plurality of accessory modules, and the plurality of therapy-providing modules are detachably connectable to the unitary command center via the interfacing ports.

31. The system of claim 1, further including the therapy-providing modules and a heat pad connected to the data processor.

32. The system of claim 1, wherein the data processor comprises a computer.

33. The system of claim 1, wherein the data processor controls provision of the therapy to the patient in response to patient information provided by at least one of the sensor modules.

* * * * *